United States Patent [19]

Heine et al.

[11] Patent Number: 4,538,889
[45] Date of Patent: Sep. 3, 1985

[54] MANUAL OPHTHALMOSCOPE

[75] Inventors: Helmut A. Heine, Herrsching; Helmut W. Rosenbusch, Weilheim; Otto H. Schmidt, Herrsching, all of Fed. Rep. of Germany

[73] Assignees: Heine Optotechnik GmbH & Co., Herrsching, Fed. Rep. of Germany; Propper Manufacturing Co., Inc., Long Island City, N.Y.

[21] Appl. No.: 445,150

[22] Filed: Nov. 29, 1982

[30] Foreign Application Priority Data

Nov. 10, 1982 [EP] European Pat. Off. ............ 82110379.3
Dec. 1, 1981 [DE] Fed. Rep. of Germany ....... 3147524

[51] Int. Cl.³ ............................................. A61B 3/10
[52] U.S. Cl. .................................... 351/205; 351/218
[58] Field of Search .............. 351/205, 206, 210, 211, 351/212, 213, 214, 233, 234, 235; 356/128, 131

[56] References Cited

U.S. PATENT DOCUMENTS 3,600,067 8/1971 Heine ................... 351/218
4,200,362 4/1980 Pomerantzeff ......... 351/16
4,407,571 10/1983 Augusto et al. .................... 351/233

FOREIGN PATENT DOCUMENTS 1940818 8/1969 Fed. Rep. of Germany .
2218681 4/1972 Fed. Rep. of Germany .
2218681 4/1972 Fed. Rep. of Germany Primary Examiner—Rodney B. Bovernick
Assistant Examiner—Paul M. Dzierzynski

[57] ABSTRACT

The inventive manual ophthalmoscope is provided with a housing 1 which is closed on all sides and in which the optical components 7, 8, 9, 13, 14 are housed in an entirely dustproof manner. The necessary switching operations for interposing correction lenses 15, 16, lighting field masks, color filters etc. into the illumination and/or observation light path 2, 3 are effected by electomagnetic drives 17, 18, 19, 20 which are adapted to be operated by means of operating elements 21, 22, 23 provided on the outside of housing 1 in optimum positions from an ergonomic point of view. The display of refraction values of correction lenses 15, 16 interposed into the observation light path as well as information deducible therefrom is effected in an optoelectronic manner.

3 Claims, 6 Drawing Figures

MANUAL OPHTHALMOSCOPE

The invention relates to a manual ophthalmoscope having an illumination system within which are interposable an imaging optical system adapted to be moved along its optical axis and/or apertures, test and measuring marks of an aperture carrier and/or the filters of a filter carrier, and having an observation light path of which are interposable the lenses within at least one lens carrier, the ophthalmoscope being provided with operating and indicating elements which are accessible or visible, respectively, from the outside of the housing.

Modern ophthalmoscopes comprise a plurality of correction lenses, lighting field masks, measuring and test marks and color filters, the adjustment of which must constantly be varied by the examiner in accordance with the purpose of the examination. The carriers of these optical elements, which are also operating elements, extend from the ophthalmoscope housing so that they can be operated directly with the fingers of the holding hand during the examination. The refraction index of the respective lenses interposed into the observation system can be read through a window provided in the housing in magnified and illuminated form. Likewise, the adjustment of the carriers of measuring and test marks as well as color filters can be read on the carrier itself or through windows.

Ophthalmoscopes of this conventional construction have the following disadvantages:

The housing apertures from which the operating elements extend permit dust particles to enter and deposit on the optical elements, thus impairing the function of the ophthalmoscope by a reduction in light power or by the imaging of dust particles in the lighting field on the eye fundus.

The arrangement of the optical elements and thus the position of the operating elements is determined less by ergonomic than by optical points of view. In almost all cases, the examiner cannot avoid having to pay an excessive amount of attention to the operation of the instrument or even to interrupt the examination.

OBJECT OF THE INVENTION

It is therefore an object of the invention to provide a manual ophthalmoscope which permits an arrangement of the operating elements which is as favorable as possible from an ergonomic point of view, and which provides safe protection of the optical elements from dust particles.

SUMMARY OF THE INVENTION

The above object is attained according to the invention by providing, within the housing, an electromagnetic or electromotoric drive for the imaging optical system and/or the aperture carrier and/or the filter carrier and/or the lens carrier, each drive being coupled to the respective carrier; by providing the operating elements on the outside of the housing without breaks or openings through the housing wall; and by providing the carriers with position detectors which are connected to respective indicating elements via signal transducers.

From U.S. Pat. No. 4,200,362 it is known to provide an electric motor for adjusting the aperture arrangement in a stationary ophthalmoscope. In that reference, however, the motor does not serve to drive the optical elements, but drives shading diaphragms adapted to suppress any excess luminosity in the peripheral zones of a photographic picture.

Since in the inventive manual ophthalmoscope of this application it is not necessary for the carriers to extend through apertures in the housing to the outside in order to be operated, the housing can be closed on all sides so that an absolutely safe dust protection is effected. Also, the operating elements can be disposed at any desired point of the housing regardless of the position of the respective carriers, at any desired point of the housing and therefore in an ergonomically optimum manner. The positions of the individual carriers and the refraction of the eye being examined as adjusted by the lens carrier can be indicated on the outside of the housing, for example, by means of a liquid crystal display.

In a preferred modification of the inventive manual ophthalmoscope, there is interposed between the operating elements and the drives an electronic control unit permitting central control of all carriers.

The limited size of a manual ophthalmoscope does not permit the accommodation in a single lens carrier of the number of lenses necessary for continuously covering a large range of corrections with a graduation of refraction values as small as possible. Use is therefore made of one or several extra lenses provided in a second carrier which may be combined with the lenses of the first carrier. An indication of the entire refraction value, in such case, is possible only with the help of complicated constructions. Instead, individual refraction values are indicated, leaving it up to the examiner to calculate the total refraction value.

Moreover, in many cases the determination of the true patient refraction on the basis of the correction value adjusted for a sharp fundus image is possible only with the help of formulas and tables. If the examiner has a visual defect and uses the ophthalmoscope without wearing his glasses, he will in addition always have to take into consideration his own refraction value. Furthermore, it is known that in determining differences in the level of the patient's eye fundus two subsequent adjustments of the correction values are carried out. Application of the rule of thumb to the effect that a difference of 3 diopters corresponds to a level difference of 1 mm may lead to errors of up to 50% in the case of patients having large visual defects.

These disadvantages are eliminated by a preferred modification of the inventive manual ophthalmoscope of this application in which the position detector or each of plural detectors of the observation system is connected to a computer, a data and instruction input for the computer being located on the outside of the housing.

With the computer programmed accordingly, the true patient refraction can easily be calculated and indicated, taking into consideration individual parameters such as the examination distance between the patient's eye and the ophthalmoscope and the examiner's refraction. Also level differences on the patient's retina can accurately be measured and indicated.

If an output of the computer is connected to the drive of the imaging optical system, a continually clear imaging of measuring and test marks on the patient's fundus can be obtained even if a plurality of lens carriers are used, which heretofore has not been possible with a reasonable amount of mechanical means unless the ophthalmoscope was equipped with only one lens carrier. Also, in the case of this embodiment, the imaging optical system, in accordance with the refraction of the patient's eye, may be moved along its optical axis in such a way that a constant imaging scale is produced on the patient's eye fundus.

Since between examinations the individual carriers of ophthalmoscopes have to be set back to their zero or neutral positions, a substantial operational simplification is attained by the use of a zero instruction input effecting an automatic and simultaneous of the carriers via the drives. In this case an optical and/or acoustic signal is provided informing the user of the completion of the set-back operation.

BRIEF DESCRIPTION OF THE DRAWINGS

The invention and further particulars will be described more specifically hereinafter with reference to a preferred embodiment shown in the drawings, in which.

DETAILED DESCRIPTION OF A PREFERRED EMBODIMENT OF THE INVENTION

Figure 1:
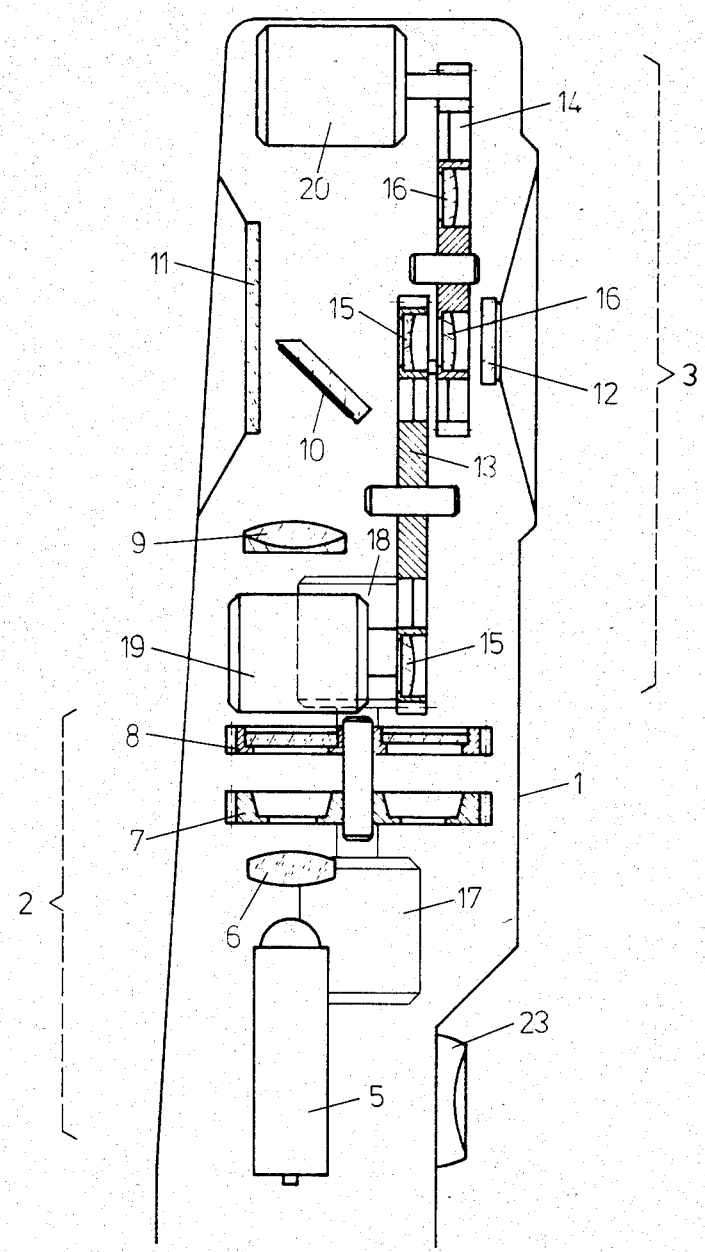
FIG. 1 shows an enlarged side elevation of a manual ophthalmoscope according to this invention with the housing partly broken apart.

According to FIG. 1, the illumination system 2 and the observation system 3 are accommodated in the housing 1 of a manual ophthalmoscope, the housing being closed on all sides.

The illumination system 2 comprises a light source 5 in the form of a lightbulb. The light source is arranged in series with a condensor 6, an aperture carrier 7 and a filter carrier 8 with their apertures, test and measuring marks and filters being respectively interposable into the light path of the illumination system 2. An optical imaging system 9 consists, if desired, of a plurality of parts which are movable relative to each other along their optical axes, and images light onto a deflectionmirror 10 which reflects the light beam through an exit window 11 to the patient's eye.

The observation system 3 comprises a viewing window 12, which may, if desired, be constituted by a lens, as well as a first lens carrier 13 for gross adjustment and a second lens carrier 14 for fine adjustment with their lenses 15 and 16, respectively, being selectively interposable into the observation light path. The refraction values of lenses 15 and 16 are respectively graduated in larger and smaller steps, for example 5 diopters and 1 diopter, respectively, so as to cover the range needed in practice. For example, the gross adjustment lens carrier 13 may contain twelve lenses ranging from +20 to −35 in steps of 5 diopters each, and the fine adjustment lens carrier 14 may contain lenses ranging between 0 and +4 in steps of 1 diopter each, in which case the range from −35 to +24 diopters can be covered in steps of 1 diopter each.

Figure 2:
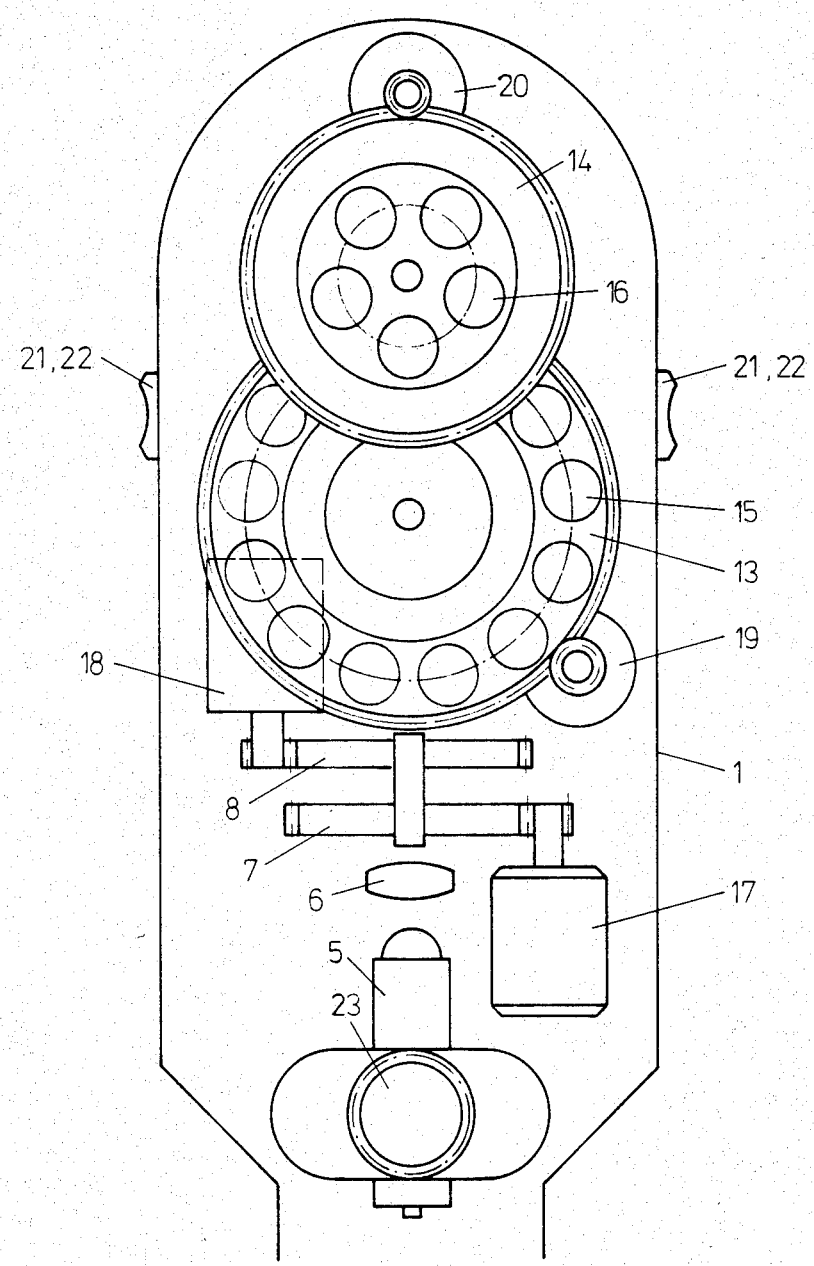
FIG. 2 shows an enlarged front elevation (as seen by the examiner) of the manual ophthalmoscope according to this invention with the housing broken apart.

According to FIGS. 1 and 2, the aperture carrier 7, the filter carrier 8 and the two lens carriers 13 and 14 each have a drive 17, 18, 19 and 20, respectively, assigned thereto. The drives may be constituted by operating magnets, step motors or the like.

Operating elements are provided on both sides of housing 1 (FIG. 2) in the form of sliding keys 21 which are movable in an upward and downward direction to operate the gross adjustment lens carrier 13; sliding keys 22 operating the fine adjustment lens carrier (not visible in FIG. 2) are disposed behind keys 21. Since identical sliding keys 21, 22 are provided on both sides of housing 1, the manual ophthalmoscope is adapted to be operated equally well by right-handed and left-handed persons. According to FIG. 2, an additional sliding key 23 may be moved to the left to adjust aperture carrier 7 or to the right to adjust filter carrier 8. By pressing sliding key 23, all of the carriers can be restored to the zero or starting positions.

Figures 3, 4, 5:
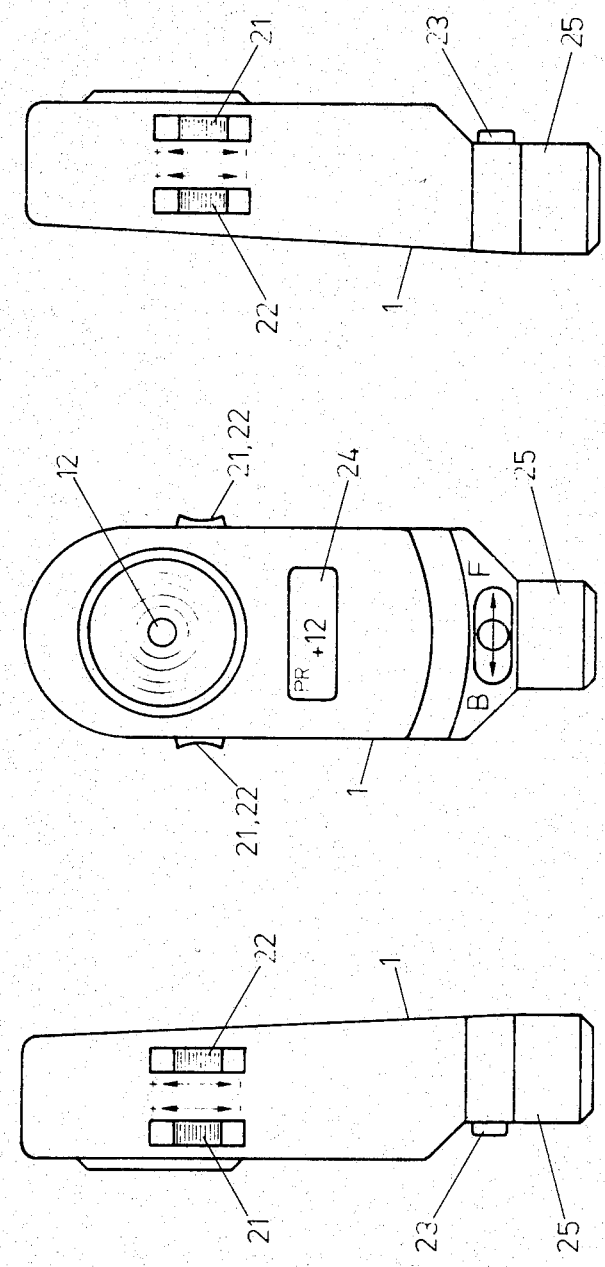
FIGS. 3, 4 and 5 respectively show the right-hand side elevation, the front elevation as seen by the examiner and the left-hand side elevation of a manual ophthalmoscope according to this invention.

FIGS. 3, 4 and 5 show the manual ophthalmoscope with housing 1 closed. Provided below viewing window 12 is a display 24, for example a liquid crystal display, showing the refraction value adjusted by means of lens carriers 13 and 14. The positions of aperture carrier 7 and filter carrier 8 may be displayed through additional viewing windows, or their positions may be shown by a display combined with display 24.

The latter display may, of course, also serve to display the results of any other calculations such as the true patient refraction taking into consideration examination parameters, the size of level differences of the eye fundus, the division of measuring marks projected onto the eye fundus, etc. Also display 24 may be used to check the inputted examination parameters.

The base 25 of the housing is designed as a current supply unit.

Figure 6:
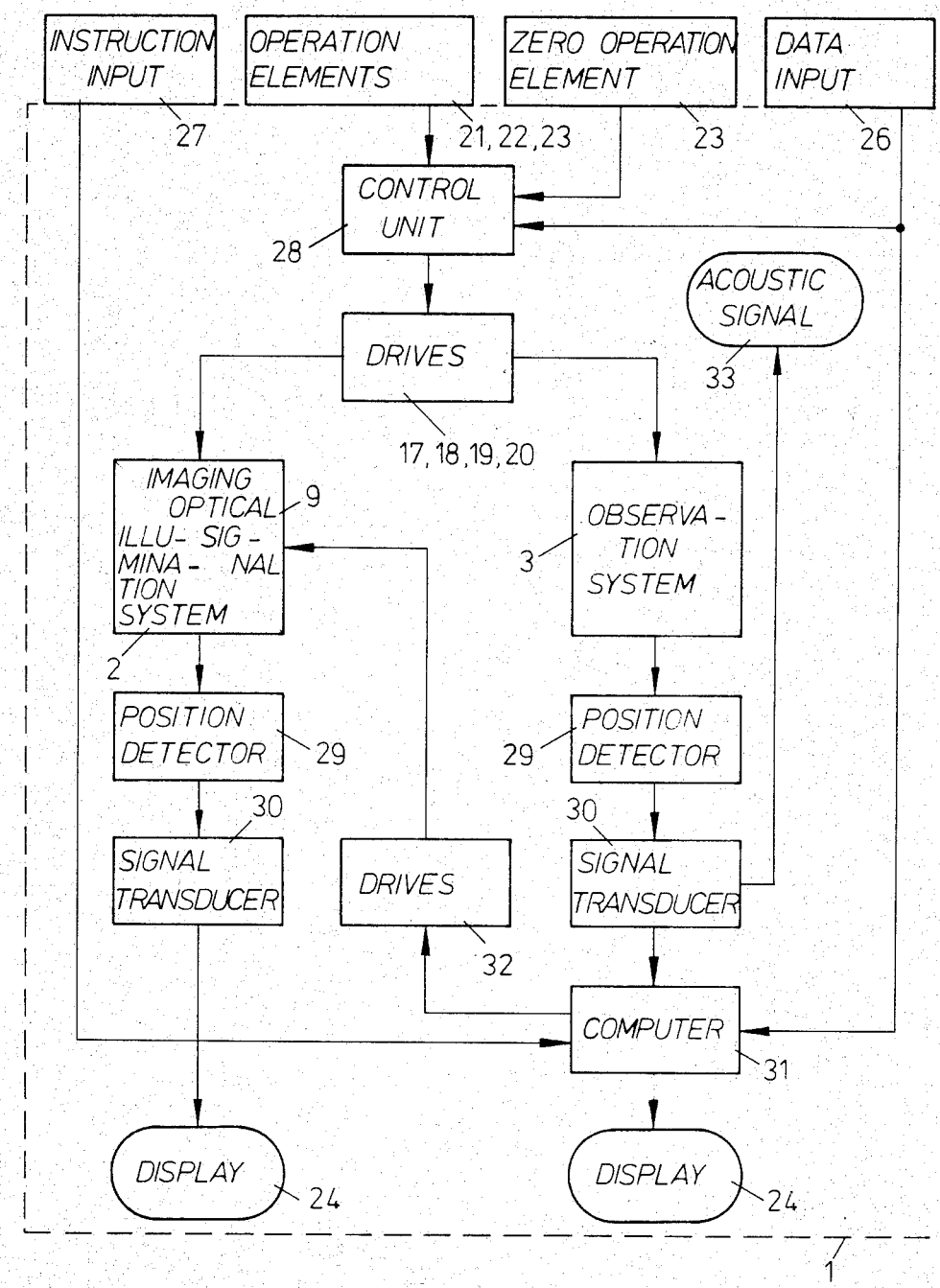
FIG. 6 shows a block diagram of the individual elements of a manual ophthalmoscope according to this invention.

According to FIG. 6, operating elements 21, 22, 23, a data input 26 and an instruction input 27 for a computer are provided on the outside of housing 1. The outputs of operating elements 21, 22, 23 are connected to an electronic control unit 28, the output of the latter in turn being connected to drives 17, 18, 19, 20. Drives 17 and 18 serve to operate aperture carrier 7 and filter carrier 8. Drives 19, 20 serve to operate the two lens carriers 13, 14 of observation system 3.

Illumination system 2 as well as observation system 3 each comprise a position detector 29 which detects the positions of the respective carriers connected in series with signal transducer 30. Although only one detector 29 and transducer 30 is illustrated, a plurality of each may be utilized. Signal transducer 30 of illumination system 2 directly controls the respective display 24, while observation system 3 has a computer 31 connected between signal transducer 30 and display 24. Two additional inputs of computer 31 are connected to data input 26 and instruction input 27, respectively. One output of computer 31 operates a drive 32 (not shown in FIGS. 1 and 2) for the carrier of the movable member of imaging optical system 9.

In the manual ophthalmoscope shown in FIG. 6, the carriers (aperture carrier 7, filter carrier 8, lens carriers 13, 14) can be adjusted in the usual manner by means of operating elements 21, 22, 23. A set-back or return to zero operation of the individual carriers can be effected by operating the zero operating element 23. The attainment of the neutral or zero position is indicated by an optical and/or acoustic signal connected to signal transducer 30 of observation system 3. By means of data input 26 and instruction input 27, any desired data and instructions may be inputted to computer 31 and programs stored in the computer may be called up. In this way it is possible by means of computer 31 to calculate the true patient refraction and also level differences of the eye fundus from the positions of lens carriers 13 and 14, taking into consideration individual examination parameters such as the distance between the ophthalmoscope and the patient's eye, the examiner's refraction, the preferred position of functional elements etc. With the help of drive 32 it is possible to guide the movable member of imaging optical system 9 in accordance with the determined true refraction value of the patient so that the built-in apertures or measuring marks may be clearly imaged on the fundus of the eye under examination. This makes it possible, for example, to indicate if necessary the imaging scale of measuring marks which varies as a function of the refraction of the eye under examination or directly the true spacing of scale divisions on the eye fundus. Also the movable member or, if desired, a plurality of such members of imaging optical system 9 may be moved along their optical axis in such a way as to obtain a constant imaging scale on the fundus.

What is claimed is:

1. An ophthalmoscope for examining a patient's eyes comprising a housing, an illumination system for directing light on the eye under examination, said illumination system located within said housing and including an illumination light path, an optical imaging system rotatable about an axis, said optical imaging system formed of a plurality of parts including at least one of apertures and measuring marks, a first motor for rotating said optical imaging system about said axis to interpose any one of said parts into said illumination light path so as to produce an image of said aperture or measuring mark on the fundus of the eye under examination, an observation system for viewing the eye under examination, said observation system located within said housing and including an observation light path, a gross adjustment lens carrier rotatable about an axis, a plurality of lenses located on said gross adjustment lens carrier, a second motor for rotating said gross adjustment lens carrier about said axis to interpose any one of said lenses into said observation light path, a fine adjustment lens carrier rotatable about an axis, a plurality of lenses located on said fine adjustment lens carrier, a third motor for rotating said fine adjustment lens carrier about said axis to interpose anyone of said lenses into said observation light path, said gross adjustment lens carrier and said fine adjustment lens carrier adapted to cooperate to provide a wide range of refraction values, position detection means located within said housing for generatng position signals corresponding to the position of said optical imaging system, said gross adjustment lens carrier and said fine adjustment lens carrier, display means visible from outside said housing and responsive to said position signals for providing a visual indication of the position of said optical imaging system, said gross adjustment lens carrier and said fine adjustment lens carrier, a plurality of operating elements accessible from outside of said housing and adapted to be operated to drive said second and third motors to respectively rotate said said gross adjustment lens carrier and said fine adjustment lens carrier, computer means located within said housing, said computer means adapted to receive the position signals corresponding to the position of said gross adjustment lens carrier and said fine adjustment lens carrier and provide an output indicative of the refraction of the eye under examination, said display means adapted to receive said output and provide a visual indication of said refraction and said computer means being in communication with and adapted to drive said first motor to achieve movement of said optical imaging system in response to said output so as to provide a constant clear image of said aperture or measuring mark of said optical imaging system on the fundus of the eye under examination notwithstanding the positions of said gross adjustment lens carrier and said fine adjustment lens carrier.

2. Apparatus as in claim 1 which further comprises an aperture carrier rotatable about an axis, a plurality of apertures located on said aperture carrier, a fourth motor for rotating said aperture carrier about said axis to interpose any one of said apertures into said ilumination light path, a filter carrier rotatable about an axis, a plurality of filters located on said filter carrier, a fifth motor for rotating said filter carrier about said axis to interpose anyone of said filters in said illumination light path, said position detection means adapted to generate position signals corresponding to the position of said aperture carrier and said filter carrier and said display means adapted to provide a visual indication of the position of said aperture carrier and said filter carrier.

3. An ophthalmoscope for examining a patient's eyes comprising a housing, an illumination system for directing light on the eye under examination, said illumination system located within said housing and including an illumination light path, an optical imaging system disposed within said illumination light path, an aperture carrier rotatable about an axis, a plurality of apertures located on said aperture carrier, a first motor for rotating said aperture carrier about said axis to interpose any one of said apertures into said ilumination light path, a filter carrier rotatable about an axis, a plurality of filters located on said filter carrier, a second motor for rotating said filter carrier about said axis to interpose anyone of said filters in said illumination light path, an observation system for viewing the eye under examination, said observation system located within said housing and including an observation light path, a gross adjustment lens carrier rotatable about an axis, a plurality of lenses located on said gross adjustment lens carrier, a third motor for rotating said gross adjustment lens carrier about said axis to interpose any one of said lenses into said observation light path, a fine adjustment lens carrier rotatable about an axis, a plurality of lenses located on said fine adjustment lens carrier, a fourth motor for rotating said fine adjustment lens carrier about said axis to interpose anyone of said lenses into said observation light path, said gross adjustment lens carrier and said fine adjustment lens carrier adapted to cooperate to provide a wide range of refraction values, position detection means located within said housing for generating position signals corresponding to the position of said optical imaging system, said aperture carrier, said filter carrier, said gross adjustment lens carrier and said fine adjustment lens carrier, display means visible from outside said housing and responsive to said position signals for providing a visual indication of the position of said aperture carrier, said filter carrier, said gross adjustment lens carrier and said fine adjustment lens carrier, a plurality of operating elements accessible from outside of said housing and adapted to be operated to drive said first, second, third and fourth motors to respectively rotate said aperture carrier, said filter carrier, said gross adjustment lens carrier and said fine adjustment lens carrier, each of said aperture carrier, filter carrier, gross adjustment lens carrier and fine adjustment lens carrier having a neutral position which position is desirable at the beginning of an examination, said plurality of operating elements further including a neutral position element adapted to be operated to drive said first, second, third and fourth motors to rotate said aperture carrier, filter carrier, gross adjustment lens carrier and fine adjustment lens carrier to their respective neutral positions.

* * * * *